US00PP13183P2

(12) United States Plant Patent
Zary

(10) Patent No.: US PP13,183 P2
(45) Date of Patent: Nov. 5, 2002

(54) FLORIBUNDA ROSE PLANT NAMED 'JACIDESO'

(75) Inventor: Keith W. Zary, Thousand Oaks, CA (US)

(73) Assignee: Jackson & Perkins Wholesale, Inc., Medford, OR (US)

( * ) Notice: Subject to any disclaimer, the term of this patent is extended or adjusted under 35 U.S.C. 154(b) by 12 days.

(21) Appl. No.: 09/695,780

(22) Filed: Oct. 24, 2000

(51) Int. Cl.[7] ..... A01H 5/00
(52) U.S. Cl. ..... Plt./143
(58) Field of Search ..... Plt./143

*Primary Examiner*—Bruce R. Campell
*Assistant Examiner*—Susan B. McCormick
(74) *Attorney, Agent, or Firm*—Klarquist Sparkman, LLP

(57) ABSTRACT

Floribunda rose plant having fragrant lavender flowers in large rounded clusters and dark, glossy green foliage having good resistance to mildew and rust.

1 Drawing Sheet

The present invention relates to a new and distinct variety of rose plant of the floribunda class which was originated by me by crossing the variety JACship (U.S. Plant Pat. No. 7,948) with the variety AROsedi (U.S. Plant Pat. No. 9,172).

The primary objective of this breeding was to produce a new rose variety having the rounded, vigorous, plant habit and large flower clusters of the female parent combined with the lavender flower color; deep green foliage; and fragrance of the male parent.

The objective was substantially achieved, along with other desirable improvements, as evidenced by the following unique combination of characteristics that are outstanding in the new variety and that distinguish it from its parents, as well as from all other varieties of which I am aware:

1. Strong fragrance;
2. Lavender flower color;
3. Large rounded clusters;
4. Dark, glossy green foliage; and
5. Good disease resistance Asexual reproduction of this new variety by budding, as performed at Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart (1966), except where ordinary dictionary significance of color is indicated.

Parentage:
*Seed parent.*—JACship (U.S. Plant Pat. No. 7,948).
*Pollen parent.*—AROsedi (U.S. Plant Pat. No. 9,172).
Classification:
*Botanical.*—*Rosa hybrida.*
*Commercial.*—Floribunda.

FLOWER

Observations made from specimens grown in a garden environment at Somis, Calif. in January 1999 through July 2000.

Blooming habit: Continuous.

Bud:

*Size.*—1¼ inch long and 3¼ inches in diameter at the base when the petals start to unfurl.

*Form.*—The bud form is long, pointed ovoid.

*Color.*—When sepals first divide, bud color is Red-Purple Group 59C with some darker edge areas where there has been exposure to bright sunlight. These areas are close to Red-Purple Group 59A. When half blown, the upper sides of the petals are Red-Purple Group 64C; and the lower sides of the petals are Red-Purple Group 64D.

*Sepals.*—Color: Green Group 138B, often with Red-Purple Group 187C in areas exposed to bright sunlight. Surface texture: Covered in fine hairs. Length: ¾ inch. Width: ⅝ inch. There are three lightly appendaged sepals. There are two unappendaged sepals with hairy edges.

*Receptacle.*—Color: Green Group 138B. Shape: Funnel. Size: Medium (about 5/16 inch×¼ inch). Surface: Smooth.

*Peduncle.*—Length: Medium (about 2 inches to 2½ inches). Surface: Glandular. Color: Green Group 138B, but where exposed to sunlight it is Greyed-Purple Group 183B. Strength: Stiff; erect.

Bloom:

*Size.*—Medium. Average open size is 3½ to 4 inches.

*Borne.*—Several together in rounded clusters of 3 to 7 blooms.

*Stems.*—Strength: Strong. Average length is about 14 to 18 inches.

*Form.*—When first open: High centered. Permanence: Flattens; outer petals curl back.

*Petalage.*—Number of petals under normal conditions: 30.

*Color.*—The upper sides of the petals are Red-Purple Group 64C. The reverse sides of the petals are Red-Purple Group 64D. The base of each petal has a ¼ inch×⅜ inch Yellow 11D color spot. The major color on the upper side is Red-Purple Group 64C.

*Variegations.*—There are Green-White Group 157D streaks along the midrib of some of the guard petals.

*Discoloration.*—The general tonality at the end of the first day: No change. At the end of the third day: No change. No change through day five when the plant color will fade to Red-Purple Group 64D. Petal drop occurs by day six.

*Fragrance.*—Strong; spicy.

Petals:

*Texture.*—Thick; leathery.

*Shape.*—Round to slighty deltoid.

*Base.*—Rounded.

*Apex.*—Obtuse.

*Form.*—Tips slightly recurved.

*Arrangement.*—Imbricated. Petaloids in the center are few (3 to 8) They are Red-Purple Group 64C, but with a Green-White Group 157D streak on one side of the petaloid or down the middle of the petaloid. Size ranges from ½ inch×¼ inch to 1 inch×½ inch.

*Persistance.*—Petals drop off cleanly before drying.

*Lastingness.*—On the plant: Fair (about 5–6 days). As a cut flower: Fair (about 6 days).

Reproductive parts:

*Anthers.*—Size: Length: 1/16–1/18 inch. Quantity: 130–160. Color: Yellow-Orange Group 19C. Arrangement: Regular around styles.

*Filaments.*—Color: Green-White Group 157D. Length: 3/16–¼ inch.

*Pistils.*—Number: 110–130.

*Pollen.*—Color: Yellow-Orange Group 20C.

*Styles.*—Color: Red Group 53C. Length: 3/16–¼ inch.

*Stigmas.*—Color: Yellow-White Group 158B. Length: 1/16 inch.

*Hips.*—None formed.

Plant:

*Form.*—Bush.

*Growth.*—Vigorous; upright; branching. At maturity, height is 3½ feet, width is 3 feet at one year of growth in a garden in Somis, Calif.

Foliage: Number of leaflets on normal mid-stem leaves: 5 to 7.

*Size.*—Large (7 inch×5 inches wide).

*Quantity.*—*Abundant.*

*Color.*—New foliage: Upper surface: Greyed-Purple Group 187A. Lower surface: Greyed-Red Group 178A. Old foliage: Upper surface: Green Group 139A. Lower surface: Green Group 139B.

Leaflets:

*Shape.*—Pointed oval.

*Size.*—Length: 1 3/16 inch. Width: 1¼ inch.

*Texture.*—Leathery; glossy.

*Edge.*—Serrated.

*Serration.*—Single; small.

*Petiole rachis.*—Color: Upper surface: Greyed-Purple Group 187A. Lower surface: Green Group 139C.

*Petiole underside.*—Rough with prickles and glands.

*Stipules.*—Medium (about ¾ inch); serrated; bearded.

*Disease resistance.*—Resistant to mildew and rust under normal growing conditions. Susceptible to blackspot.

*Venation pattern.*—Costate.

*Vein on lower surface.*—Color: Green Group 139B.

Wood:

*New wood.*—Color: Green Group 137D with a Greyed-Purple Group 183B color when exposed to bright sunlight. Bark: Smooth.

*Old wood.*—Color: Green Group 137A. Bark: Smooth.

Prickles:

*Quantity.*—On main canes from base: Ordinary. On laterals from main canes: Ordinary.

*Form.*—Medium; hooked downward.

*Length.*—¼ inch.

*Color when young.*—Greyed-Purple Group 183B.

*Color when mature.*—Greyed-Orange Group 173C.

Small prickles:

*Quantity.*—On main stalks: Many to few. On large basal canes, small prickles are numerous. On laterals: Small prickles are generally few.

*Color.*—Greyed-Red Group 183B when young, but are Greyed-Orange Group 165A when mature.

I claim:

1. A new and distinct variety of rose plant of the floribunda class, substantially as herein shown and described, characterized particularly by its lavender flowers in large rounded clusters, and having strong fragrance and its dark, glossy green foliage having good resistance to mildew and rust.

* * * * *

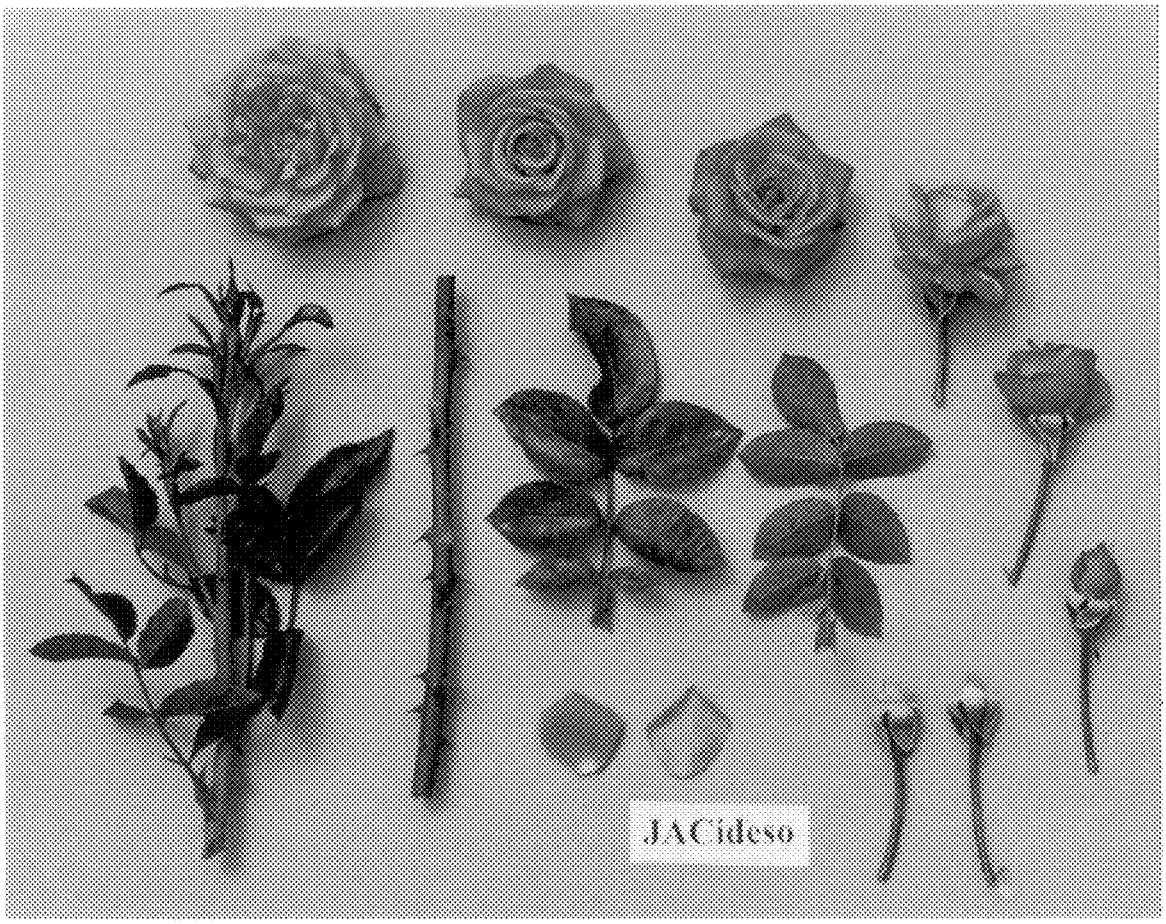
JACideso